United States Patent [19]

Hesse

[11] Patent Number: Plant 6,775

[45] Date of Patent: May 2, 1989

[54] CHRYSANTHEMUM PLANT NAMED TITAN

[75] Inventor: Peter S. Hesse, Bradenton, Fla.

[73] Assignee: Ball Seed Company, West Chicago, Ill.

[21] Appl. No.: 139,731

[22] Filed: Dec. 30, 1987

[51] Int. Cl.[4] ..... A01H 5/00

[52] U.S. Cl. ..... Plt./77

[58] Field of Search ..... Plt./77

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Titan having white ray florets which are yellow in center and which do not pink with age, 8 week flowering response, compact cushion plant habit, very floriferous habit, and its suitability for garden mum production in varying size containers.

1 Drawing Sheet

The present invention comprises a new and distinct cultivar of *Chrysanthemum morifolium,* hereinafter referred to by the cultivar name Titan.

Titan is a product of a planned breeding program which had the objective of creating new Chrysanthemum cultivars having compact habit, early flower response, excellent flower quality, white decorative flowers, and suitability for production as a garden mum. Such traits in combination were not present or needed improvement in previously available commercial cultivars.

Titan was originated from a hybridization made by applicant in a controlled breeding program in Parrish, Fla. in 1982. The female parent was Husky, disclosed in U.S. Plant Pat. No. 4,753. The male parent of Titan was Freedom, disclosed in U.S. Plant Pat. No. 3,898. Titan was discovered and selected as one flowering plant within the progeny of the stated parentage by applicant in November 1982 in a controlled environment in Parrish, Fla.

The first act of asexual reproduction of Titan was accomplished when vegetative cuttings were taken from the initial selection in March 1983 in a controlled environment in Parrish, Fla. by a technician working under formulations established and supervised by applicant. Horticultural examination of selected units initiated in October 1983 has demonstrated that the combination of characteristics as herein disclosed for Titan are firmly fixed and are retained through successive generations of asexual reproduction.

The following traits have been repeatedly observed and are determined to be basic characteristics of Titan, which in combination distinguish this Chrysanthemum as a new and distinct cultivar:

1. Eight week flowering response.
2. Almost fully double flower form.
3. White ray florets, which are non-pinking a flowers age, and which have yellow centers.
4. Ray florets are up to 2.8 cm long and 9 mm wide.
5. Total flower diameter reaches 5.5 cm.
6. Compact cushion plant habit.
7. Very floriferous, producing a large mass of long lasting flowers.
8. Suitable for use as a garden mum for production in 4½" to 1 gallon containers.

Titan has not been observed under all possible environmental conditions. The phenotype may vary significantly with variations in environment such as temperature, light intensity, and day length. The following observations, measurements and comparisons describe plants grown in Parrish, Fla. under greenhouse conditions which approximate those generally used in commercial practice.

Of the many commercial cultivars known to the present inventor, the most similar in comparison to Titan is Patriot, disclosed in U.S. Plant Pat. No. 3,897. In comparison to Patriot, Titan has a two (2) week later flower response and the ray florets are non-pinking as the flowers mature. The cushion habit and white decorative flowers of Titan are similar to those same characteristics of Patriot.

The accompanying photographic drawing shows typical inflorescence and foliage characteristics of Titan. The photographic drawing comprises a black and white photograph with a few flowers and leaves being colored to depict true color.

In the following description, color references are made to The Royal Horticultural Society Colour Chart. The color values were determined between 11:00 and 11:15 a.m. on Oct. 21, 1987 under fluorescent light at Parrish, Fla.

Classification:

*Botanical.*—*Chrysanthemum morifolium,* cv. Titan.

*Commercial.*—Decorative garden mum.

INFLORESCENCE

A. Capitulum:

*Form.*—Flat.

*Type.*—Double.

*Diameter across face.*—Up to 5.5 cm.

B. Corolla of ray florets:

*Color (general tonality from a distance of three meters).*—White.

*Color (upper and lower surfaces).*—155D, with the petals near the center being varying shades of 4A to 4D, with the more intense 4A appearing at the center.

C. Corolla of disc florets:

*Color (mature).*—Yellow (very few present).

*Color (immature).*—Yellow-green (very few present).

D. Reproductive organs:

*Androecium.*—Present in disc florets only.

*Gynoecium.*—Present in both disc and ray florets.

PLANT

A. General appearance:

*Height.*—Approximately 25 cm when grown in the ground, given no long days and one pinch. Height will vary depending upon growing conditions.

B. Foliage:

*Color* (*upper surface*).—147A.

*Color* (*lower surface*).—147B.

*Shape.*—Ovate, deeply lobed and slightly serrate margins.

I claim:

1. A new and distinct cultivar of Chrysanthemum plant named Titan, as illustrated and described, and parts thereof.

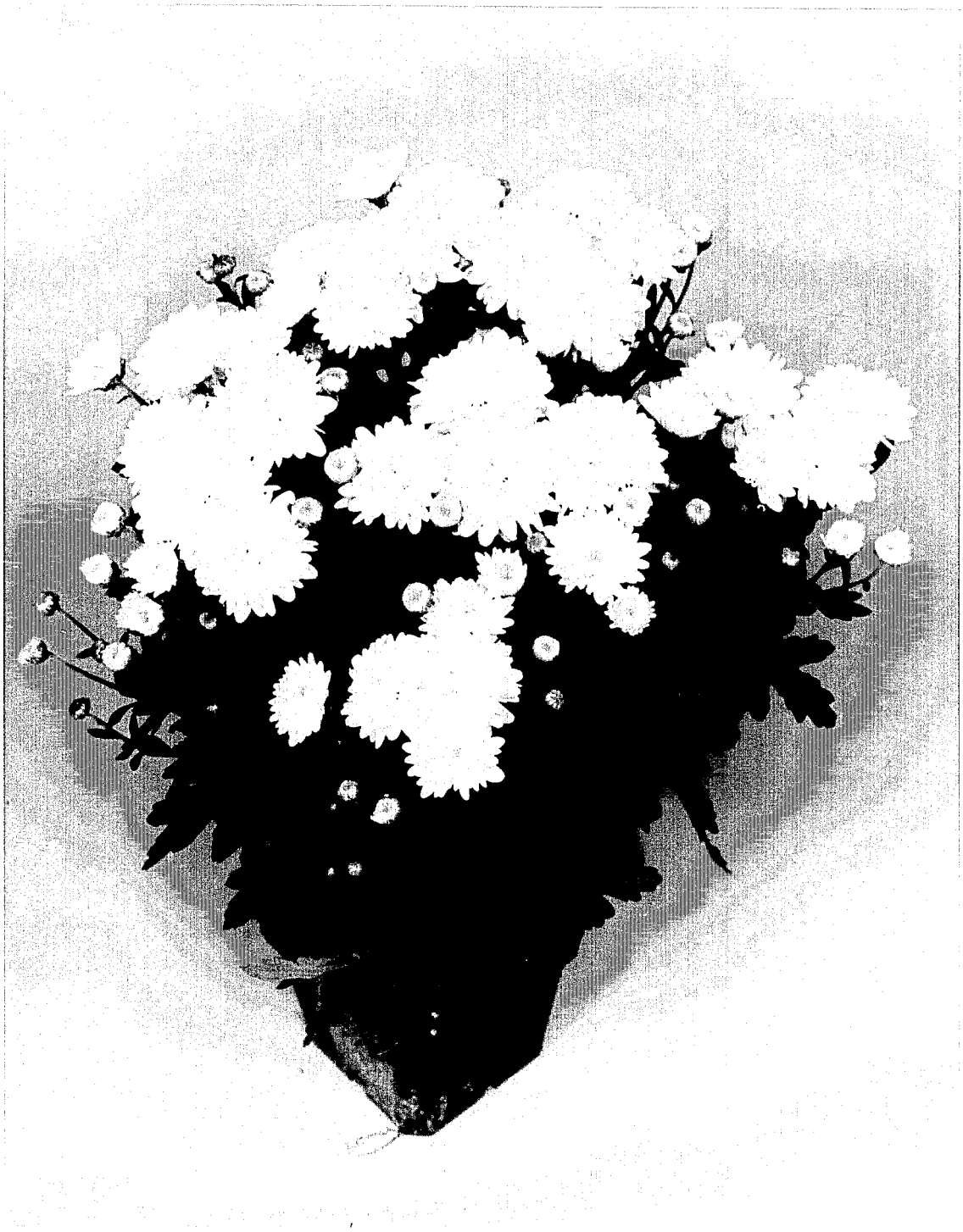

* * * * *